Figure 1:
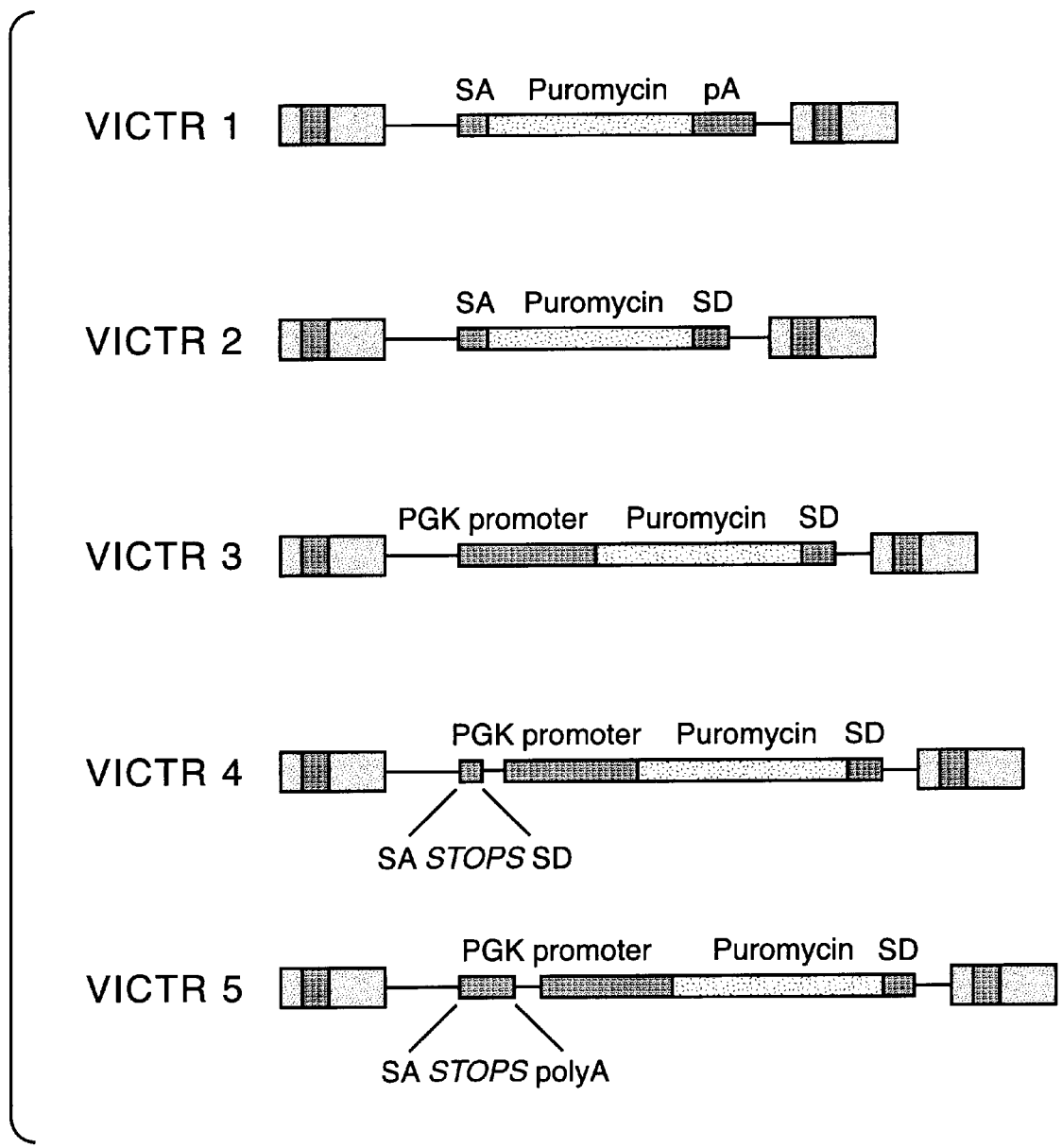

United States Patent [19]
Sands et al.

[11] Patent Number: 6,136,566
[45] Date of Patent: *Oct. 24, 2000

[54] INDEXED LIBRARY OF CELLS CONTAINING GENOMIC MODIFICATIONS AND METHODS OF MAKING AND UTILIZING THE SAME

[75] Inventors: Arthur Sands; Glenn Friedrich; Brian Zambrowicz, all of The Woodlands; Allan Bradley, Houston, all of Tex.

[73] Assignee: Lexicon Graphics Incorporated, The Woodlands, Tex.

[*] Notice: This patent is subject to a terminal disclaimer.

[21] Appl. No.: 08/726,867

[22] Filed: Oct. 4, 1996

[51] Int. Cl.$^7$ ............... C12P 21/00; C12N 15/63; C12N 5/00; C07H 21/04

[52] U.S. Cl. ............... 435/69.7; 435/320.1; 435/325; 435/352; 435/455; 536/23.4; 536/24.1

[58] Field of Search ............... 435/6, 91.4, 320.1, 435/325, 352, 69.7, 172.3, 455; 536/23.4, 24.1

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.2 |
| 5,449,614 | 9/1995 | Danos et al. | 435/457 |
| 5,464,764 | 11/1995 | Capecchi et al. | 435/6 |
| 5,641,670 | 6/1997 | Treco et al. | 435/252.3 |

FOREIGN PATENT DOCUMENTS

| | | |
|---|---|---|
| WO88/01646 | 3/1988 | WIPO . |
| WO 98/20031 | 5/1998 | WIPO . |
| WO 98/24918 | 6/1998 | WIPO . |

OTHER PUBLICATIONS

Sauer. Site–specific recombination:developments and applications. Curr. Opin. Biotechnol. vol. 5:521–527, May 1994.

Sekine et al. Frameshifting is required for production of the transposase encoded by insertion sequence 1. PNAS (USA) vol. 86:4609–4612, Jun. 1989.

Wang et al. High frequency recombination between loxP sites in human chromosomes mediated by an adenovirus vector expressing Cre recombinase. Somatic Cell and Mol. Genet. vol. 21(6):429–441, Mar. 9, 1996.

Haas et al. TnMax–a versatile minitransposon for teh analysis of cloned genes and shuttle mutagenesis. Gene vol. 130:23–31, Aug. 11, 1993.

Odell et al. Site–directed recombination in the genome of transgenic tobacco. Mol. Gen. Genet. Vol. 223:369–378, Oct. 11, 1990.

Dymecki. A modular set of Flp, FRT and LacZ fusion vectors for manipulating genes by site–specific recombination. Gene. vol. 171:197–201, Jun. 1, 1996.

Auch et al. Exon trap cloning: using PCR to rapidly detect and clone exons from genomic DNA fragments. Nucleic Acids Res. vol. 18(22):6743–6744, Nov. 22, 1990.

Duyk et al. Exon trapping: A genetic screen to identify candidate transcribed sequences in cloned mammalian genomic DNA. PNAS (USA) vol. 87:8995–8999, Nov. 1990.

Reilly et al. Trascription vectors that facilitate the identification and mapping of RNA splice sites in genomic DNA. DNA and Cell Biology vol. 9(7):535–542, Jul. 1990.

Nussaume et al. Analysis of splice donor and acceptor site function in a transposable gene trap derived from the maize element activator. Mol. Gen. Genet. vol. 249:91–101, Dec. 18, 1995.

Allen et al., 1988, "Transgenes as probes for active chromosomal domains in mouse development", Nature 333(6176):852–855.

Altschul et al., 1990, "Basic Local Alignment Search Tool", J. Mol. Biol. 215:403–410.

Bellen et al., 1989, "P–element–mediated enhancer detection: a versatile method to study development in Drosophila", Genes Dev. 3:1288–1300.

Bier et al., 1989, "Searching for pattern and mutation in the Drosophila genome with a P–lacZ vector", Genes Dev. 3:1273–1287.

Bonnerot et al., 1992, "Capture of a Cellular Transcriptional Unit by a Retrovirus: Mode of Provirus Activation in Embryonal Carcinoma Cells", J. Virol. 66:4982–4991.

Bradley, 1991, "Modifying the mammalian genome by gene targeting", Cur. Opin. Biotech. 2:823–829.

Brenner et al., 1989, "Analysis of mammalian cell genetic regulation in situ by using retrovirus–derived "portable exons" carrying the *Escherichia coli* lacZ gene ", Proc. Natl. Acad. Sci. U.S.A. 86:5517–5521.

Chang et al., 1993, "Enrichment of Insertional Mutants Following Retrovirus Gene Trap Selection", Virology 193:737–747.

(List continued on next page.)

*Primary Examiner*—David Guzo
*Assistant Examiner*—William Sandals
*Attorney, Agent, or Firm*—Finnegan, Henderson, Farabow, Garrett & Dunner

[57] ABSTRACT

Methods and vectors (both DNA and retroviral) are provided for the construction of a Library of mutated cells. The Library will preferably contain mutations in essentially all genes present in the genome of the cells. The nature of the Library and the vectors allow for methods of screening for mutations in specific genes, and for gathering nucleotide sequence data from each mutated gene to provide a database of tagged gene sequences. Such a database provides a means to access the individual mutant cell clones contained in the Library. The invention includes the described Library, methods of making the same, and vectors used to construct the Library. Methods are also provided for accessing individual parts of the Library either by sequence or by pooling and screening. The invention also provides for the generation of non-human transgenic animals which are mutant for specific genes as isolated and generated from the cells of the Library.

23 Claims, 6 Drawing Sheets

OTHER PUBLICATIONS

Chen et al., 1994, "Transcriptional enhancer factor 1 disruption by a retroviral gene trap leads to heart defects and embryonic lethality in mice", Genes Devel. 8:2293–2301.

Friedrich and Soriano, 1993, Insertional mutagenesis by retroviruses and promoter traps in embryonic stem cells, pp. 681–701. In Methods Enzymol., vol. 225., P. M. Wassarman and M. L. DePamphilis (ed.), Academic Press, Inc., San Diego.

Friedrich and Soriano, 1991, "Promoter traps in embryonic stem cells: a genetic screen to identify and mutate developmental genes in mice", Genes Dev. 5:1513–1523.

Frohman et al., 1988, "Rapid production of full–length dCNAs from rare transcripts: Amplification using a single gene–specific oligonucleotide primer", Proc. Natl. Acad. Sci. U.S.A. 85:8998–9002.

Goff, 1987, "Gene Isolation by Retroviral Tagging", Methods Enzymol. 152:469–481.

Gossler et al., 1989, "Mouse Embryonic Stem Cells and Reporter Constructs to Detect Developmentally Regulated Genes", Science 244:463–465.

Hope, 1991, "'Promoter trapping' in Caenorhabditis elegans", Develop. 113:399–408.

Kerr et al., 1989, "Transcriptionally Defective Retroviruses Containing lacZ for the In Situ Detectioin of Endogenous Genes and Developmentally Regulated Chromatin", Cold Spring Harb. Symp. Quant. Biol. 2:767–776.

Kozak, 1989, "The Scanning Model for Translation: An Update", J. Cell, Biol. 108:229–241.

Reddy et al., 1992, "Fluorescence–activated sorting of totipotent embryonic stem cells expressing developmentally regulated lacZ fusion genes", Proc. Natl. Acad. Sci. U.S.A. 89:6721–6725.

Reddy et al., 1991, "Retrovirus Promoter–Trap Vector To Induce lacZ Gene Fusions in Mammalian Cells", J. Virol. 65:1507–1515.

Skarnes et al., 1992, "A gene trap approach in mouse embryonic stem cells: the lacZ reporter is activated by splicing, reflects endogenous gene expression, and is mutagenic in mice", Genes Dev. 6:903–918.

von Melchner and Ruley, 1989, "Identification of Cellular Promoters by Using a Retrovirus Promoter Trap", J. Virol. 63:3227–3233.

Yoshida et al., 1995, "A new strategy of gene trapping in ES cells using 3'Race", Transgen. Res. 4:277–287.

Campbell et al., 1997, "Totipotency or Multipotentiality of Cultured Cells: Applications and Progress", *Theriogenology* 47:63–72.

Chang et al., 1993, "Enrichment of Insertional Mutants Following Retrovirus Gene Trap Selection", *Virology* 193:737–747.

Evans et al., 1997, "Gene trapping and functional genomics", *TIG 13(9):370–374*.

Gogos et al., 1997, "Selection for Retroviral Insertions into Regulated Genes", *Journal of Virology* 71(2): 1644–1650.

Gogos et al., 1996, "Gene Trapping in Differentiating Cell Lines: Regulation of the Lysosomal Protease Cathepsin B in Skeletal Myoblast Growth and Fusion", *Journal of Cell Biology* 134(4):837–847.

Hicks et al., 1997, "Functional genomics in mice by tagged sequence mutagenesis", *Nature Genetics* 16:338–344.

Jönsson et al., 1996, "Use of a Promoter–Trap Retrovirus to Identify and Isolate Genes Involved in Differentiation of a Myeloid Progenitor Cell Line In Vitro", *Blood* 87(5): 1771–1779.

Niwa et al., 1993, "An Efficient Gene–Trap Method Using Poly A Trap Vectors and Characterization of gene–trap events", *J. Biochem 113(3):343–349*.

Skarnes, 1993, "The Identification of new genes: gene trapping in transgenic mice", *Current Opinion in Biotechnology* 4:684–689.

Zambrowicz et al., 1997, "Disruption of overlapping transcripts in the ROSA βgeo 26 gene trap strain leads to widespread expression of β–galactosidase in mouse embryos and hematopoietic cells", *Proc. Natl. Acad. Sci. USA* 94:3789–3794.

Identify Positive Pool

To screen all mouse genes (~100,000) with 5-fold redundancy would require about 50 plates of 96-wells (at 100 clones/well).

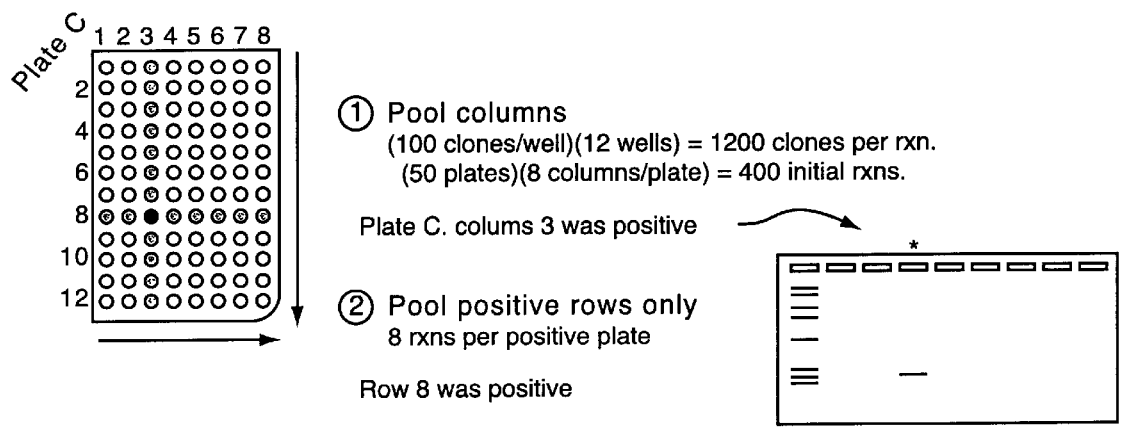

① Pool columns
(100 clones/well)(12 wells) = 1200 clones per rxn.
(50 plates)(8 columns/plate) = 400 initial rxns.

Plate C. colums 3 was positive

② Pool positive rows only
8 rxns per positive plate

Row 8 was positive

Identify Positive Clone

The pool on plate C, column 3, row 8 is thawed and plated as single clones:

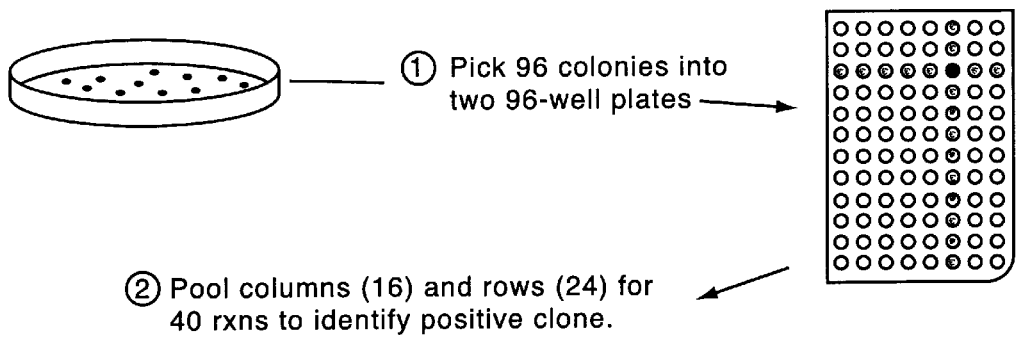

① Pick 96 colonies into two 96-well plates

② Pool columns (16) and rows (24) for 40 rxns to identify positive clone.

FIG. 5

```
OST1:                    248 TTTATATAATATTTAATTTGTTTACTGGGGTATATATGTGTGAAGAGGACTTCT 302
                             ||||                |||||||||||||||||||||||||||||||||||
rat GABA rho3:          1547 TTTACATAATATTTAATTTGTTTACTGGGGTATATATGTGTGAAGAGGACTTTT 1601

OST2:                     56 ACCGTTGCGGAGGCTCACGTTTCTCAGATAGTACATCAGGTGTCATCGNTGTCAGAAGGT 115
                             ||||||||| ||||| ||||||||||||||||||||||||||||| || |||||||||||
mouse TCR-ATF1:           75 ACCGTTGCGGGGGCCTCACGTTTCTCAGATAGTACATCAGGTGTCATCGTTATCAGAAAGT 134

OST3:                     58 GIGMHHAGLHERDRKTVEELFXNCKVQVLIATSTLAWGVNFPAHLVIIKGTEYDGKTRR 237
                             GIG+ HHAGL ++DR      +LF    K+Q+L IATSTLAWGVN  PAHLV I IKGT+++D K
Yeast ORF G9365:        1430 GIGLHHAGLVQKDRSISHQLFQKNKIQILIATSTLAWGVNLPAHLVIIKGTQFFDAKIEG 1489

OST4:                    137 GCGCAGAAGTGGTNCTGAANTTNTCCGCNCCATCCAGTCTATTAATTGTTGACNGGA 196
                             ||||||||||||| ||||| |||  ||| |||||||||||||||||||||||| ||||
seq. from US             166 GCGCAGAAGTGGTCCTGCAACTTTATCCGCCTCCAGTCTATTAATTGTTGCCGGGA 225
patent 5470724:

OST5:                    108 TCWIRLGT*RXVGASLEYEYIRAS 179
                             TCW++L     R VG  +L+ +Y  A+
mouse wnt-5A             250 TCWLQLADFRKVGDALKEKYDSAA 273
protein precursor:

OST6:                     78 CTTATATGGCTACGGCGGCTTCAACATCTCAATTACACCCAACTACAGCGTGTCCAGGCT 137
                             |||||||||||||||| ||||||||| ||   ||  || ||||||||||||||| |||||
human prolyl           1407 CTTATATGGCTATGGCGGCTTCAACATATCCATCACACCAACTACAGTGTTTCCAGGCT 1466
endopeptidase:

OST7:                    109 AAAGCATGTAGCAGTTGTAGGACACACTAGACGAGAGCACCAGATCTCATTGTGGGTGGT 168
                             ||||||||| ||||||||||||||||||||||||||||||||||||||||||||||||||
mouse                  1604 AAAGCATGCAGCAGTTGTAGGACACACTAGACGAGAGCACCAGATCTCATTGTGGGTGGT 1663
45S pre rRNA:

OST8:                    161 TGGATGCAGNCTACCACTGTGTGGCTGCCTGCAGAAGTCCAGAAAATACAGACCAAAGTGCCTCAGTTCTGGAAG 220
                             ||||||||| |||||||||||||||||||| |||||||||||||||||||||||||||||||||||| |||||||
rat MAL:                 306 TGGATGCAGCCTACCACTGTGTGGCTGCCCTGCAGAAGTCCAGAAAATACAGACCAAAGTCCTCAGTTCTGGAAG 365

OST9:                    103 ACCTGATTGTTATCCGTGGCCTGCAGAAGTCCAGAAATACAGACCAAAGTCAACCAGTA 162
                             |||||||||||||||||||||||||||||||||||| |||||||||||||||||||||||
mouse malic enzyme:    1666 ACCTGATTGTTATCCGTGGCCTGCAGAAGTCCAGAAGTACAGACCAAAGTCAACCAGTA 1725
```

FIG. 6

```
                              SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
         (A) LENGTH: 55 base pairs
         (B) TYPE: nucleic acid
         (C) STRANDEDNESS: single
         (D) TOPOLOGY: linear (xi) SEQUENCE DESCRIPTION: SEQ ID NO:1:

TTTATATAAT ATTTAATTTG TTTTACTGGG GTATATATGT GTGAAGAGGA CTTCT             55

(2) INFORMATION FOR SEQ ID NO:2:

(i) SEQUENCE CHARACTERISTICS:
         (A) LENGTH: 55 base pairs
         (B) TYPE: nucleic acid
         (C) STRANDEDNESS: single
         (D) TOPOLOGY: linear (xi) SEQUENCE DESCRIPTION: SEQ ID NO:2:

TTTACATAAT ATTTAATTTG TTTTACTGGG GTATATATGT GTGAAGAGGA CTTTT             55

(2) INFORMATION FOR SEQ ID NO:3:

(i) SEQUENCE CHARACTERISTICS:
         (A) LENGTH: 60 base pairs
         (B) TYPE: nucleic acid
         (C) STRANDEDNESS: single
         (D) TOPOLOGY: linear (xi) SEQUENCE DESCRIPTION: SEQ ID NO:3:

ACCGTTGCGG AGGCTCACGT TTCTCAGATA GTACATCAGG TGTCATCGNT GTCAGAAGGT        60

(2) INFORMATION FOR SEQ ID NO:4:

(i) SEQUENCE CHARACTERISTICS:
         (A) LENGTH: 60 base pairs
         (B) TYPE: nucleic acid
         (C) STRANDEDNESS: single
         (D) TOPOLOGY: linear (xi) SEQUENCE DESCRIPTION: SEQ ID NO:4:

ACCGTTGCGG GGCCTCACGT TTCTCAGATA GTACATCAGG TGTCATCGTT ATCAGAAAGT        60

(2) INFORMATION FOR SEQ ID NO:5:

(i) SEQUENCE CHARACTERISTICS:
         (A) LENGTH: 60 amino acids
```

(B) TYPE: amino acid
                (C) STRANDEDNESS: single
                (D) TOPOLOGY: linear (ii) MOLECULE TYPE: None (xi) SEQUENCE DESCRIPTION: SEQ ID NO:5:

Gly Ile Gly Met His His Ala Gly Leu His Glu Arg Asp Arg Lys Thr
1               5                   10                  15

Val Glu Glu Leu Phe Xaa Asn Cys Lys Val Gln Val Leu Ile Ala Thr
                20                  25                  30

Ser Thr Leu Ala Trp Gly Val Asn Phe Pro Ala His Leu Val Ile Ile
            35                  40                  45

Lys Gly Thr Glu Tyr Tyr Asp Gly Lys Thr Arg Arg
50                      55                  60

(2) INFORMATION FOR SEQ ID NO:6:

(i) SEQUENCE CHARACTERISTICS:
                (A) LENGTH: 60 amino acids
                (B) TYPE: amino acid
                (C) STRANDEDNESS: single
                (D) TOPOLOGY: linear (ii) MOLECULE TYPE: None (xi) SEQUENCE DESCRIPTION: SEQ ID NO:6:

Gly Ile Gly Leu His His Ala Gly Leu Val Gln Lys Asp Arg Ser Ile
1               5                   10                  15

Ser His Gln Leu Phe Gln Lys Asn Lys Ile Gln Ile Leu Ile Ala Thr
                20                  25                  30

Ser Thr Leu Ala Trp Gly Val Asn Leu Pro Ala His Leu Val Ile Ile
            35                  40                  45

Lys Gly Thr Gln Phe Phe Asp Ala Lys Ile Glu Gly
50                      55                  60

(2) INFORMATION FOR SEQ ID NO:7:

(i) SEQUENCE CHARACTERISTICS:
                (A) LENGTH: 60 base pairs
                (B) TYPE: nucleic acid
                (C) STRANDEDNESS: single
                (D) TOPOLOGY: linear (xi) SEQUENCE DESCRIPTION: SEQ ID NO:7:

GCGCAGAAGT GGTNCTGGAA NTTTNTCCGC CNCCATCCAG TCTATTAATT GTTGACNGGA        60

(2) INFORMATION FOR SEQ ID NO:8:

(i) SEQUENCE CHARACTERISTICS:
                (A) LENGTH: 60 base pairs
                (B) TYPE: nucleic acid
                (C) STRANDEDNESS: single
                (D) TOPOLOGY: linear (xi) SEQUENCE DESCRIPTION: SEQ ID NO:8:

GCGCAGAAGT GGTCCTGCAA CTTTATCCGC CTCCATCCAG TCTATTAATT GTTGCCGGGA        60

(2) INFORMATION FOR SEQ ID NO:9:

(i) SEQUENCE CHARACTERISTICS:
                (A) LENGTH: 23 amino acids
                (B) TYPE: amino acid
                (C) STRANDEDNESS: single
                (D) TOPOLOGY: linear (ii) MOLECULE TYPE: None (xi) SEQUENCE DESCRIPTION: SEQ ID NO:9:

Thr Cys Trp Ile Arg Leu Gly Thr Arg Xaa Val Gly Ala Ser Leu Glu
1               5                   10                  15

Tyr Glu Tyr Ile Arg Ala Ser
            20

(2) INFORMATION FOR SEQ ID NO:10:

(i) SEQUENCE CHARACTERISTICS:
        (A) LENGTH: 24 amino acids
        (B) TYPE: amino acid
        (C) STRANDEDNESS: single
        (D) TOPOLOGY: linear (xi) SEQUENCE DESCRIPTION: SEQ ID NO:10:

Thr Cys Trp Leu Gln Leu Ala Asp Phe Arg Lys Val Gly Asp Ala Leu
1               5                   10                  15

Lys Glu Lys Tyr Asp Ser Ala Ala
            20

(2) INFORMATION FOR SEQ ID NO:11:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:11:

CTTATATGGC TACGGCGGCT TCAACATCTC CATTACACCC AACTACAGCG TGTCCAGGCT        60

(2) INFORMATION FOR SEQ ID NO:12:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:12:

CTTATATGGC TATGGCGGCT TCAACATATC CATCACACCC AACTACAGTG TTTCCAGGCT        60

(2) INFORMATION FOR SEQ ID NO:13:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:13:

AAAGCATGTA GCAGTTGTAG GACACACTAG ACGAGAGCAC CAGATCTCAT TGTGGGTGGT        60

(2) INFORMATION FOR SEQ ID NO:14:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:14:

AAAGCATGTA GCAGTTGTAG GACACACTAG ACGAGAGCAC CAGATCTCAT TGTGGGTGGT        60

(2) INFORMATION FOR SEQ ID NO:15:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:15:

TGGATGCAGN CTACCACTGT GTGGCTGCCC TATTTTACCT CAGTGCCTCA GTTCTGGAAG    60

(2) INFORMATION FOR SEQ ID NO:16:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:16:

TGGATGCAGC CTACCACTGT GTGGCTGCCC TGTTTTACCT CAGTGCCTCA GTCCTGGAAG    60

(2) INFORMATION FOR SEQ ID NO:17:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:17:

ACCTGATTGT TATCCGTGGC CTGCAGAAGT CCAGAAAATA CAGACCAAAG TCAACCAGTA    60

(2) INFORMATION FOR SEQ ID NO:18:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:18:

ACCTGATTGT TATCCGTGGC CTGCAGAAGT CCAGAAAATA CAGACCAAAG TCAACCAGTA    60

INDEXED LIBRARY OF CELLS CONTAINING GENOMIC MODIFICATIONS AND METHODS OF MAKING AND UTILIZING THE SAME

1.0 FIELD OF THE INVENTION

The invention relates to an indexed library of genetically altered cells and methods of organizing the cells into an easily manipulated and characterized Library. The invention also relates to methods of making the library, vectors for making insertion mutations in genes, methods of gathering sequence information from each member clone of the Library, and methods of isolating a particular clone of interest from the Library.

2.0 BACKGROUND OF THE INVENTION

The general technologies of targeting mutations into the genome of cells, and the process of generating mouse lines from genetically altered embryonic stem (ES) cells with specific genetic lesions are well known (Bradley, 1991, Cur. Opin. Biotech. 2:823–829). A random method of generating genetic lesions in cells (called gene, or promoter, trapping) has been developed in parallel with the targeted methods of genetic mutation (Allen et al., 1988 Nature 333(6176):852–855; Brenner et al., 1989, Proc. Natl. Acad. Sci. U.S.A. 86(14):5517–5521; Chang et al., 1993, Virology 193(2):737–747; Friedrich and Soriano, 1993, Insertional mutagenesis by retroviruses and promoter traps in embryonic stem cells, p. 681–701. In Methods Enzymol., vol. 225., P. M. Wassarman and M. L. DePamphilis (ed.), Academic Press, Inc., San Diego; Friedrich and Soriano, 1991, Genes Dev. 5(9):1513–1523; Gossler et al., 1989, Science 244 (4903):463–465; Kerr et al., 1989, Cold Spring Harb. Symp. Quant. Biol. 2:767–776; Reddy et al., 1991, J Virol. 65(3):1507–1515; Reddy et al., 1992, Proc. Natl. Acad. Sci. U.S.A. 89(15):6721–6725; Skarnes et al., 1992, Genes Dev. 6(6):903–918; von Melchner and Ruley, 1989, J. Virol. 63(8):3227–3233; Yoshida et al., 1995, Transgen. Res. 4:277–287). Gene trapping provides a means to create a collection of random mutations by inserting fragments of DNA into transcribed genes. Insertions into transcribed genes are selected over the background of total insertions since the mutagenic DNA encodes an antibiotic resistance gene or some other selectable marker. The selectable marker lacks its own promoter and enhancer and must be expressed by the endogenous sequences that flank the marker after it has integrated. Using this approach, transcription of the selectable marker is activated and the cell gene is concurrently mutated. This type of strict selection makes it possible to easily isolate thousands of ES cell colonies, each with a unique mutagenic insertion.

Collecting mutants on a large-scale has been a powerful genetic technique commonly used for organisms which are more amenable to such analysis than mammals. These organisms, such as Drosophila melanogastor, yeast Saccharomyces cerevisiae, and plants such as Arabadopsis thalia are small, have short generation times and small genomes (Bellen et al., 1989, Genes Dev. 3(9):1288–1300; Bier et al., 1989, Genes Dev. 3(9):1273–1287; Hope, 1991, Develop. 113(2):399–408. These features allow an investigator to rear many thousands or millions of different mutant strains without requiring unmanageable resources. However, these type of organisms have only limited value in the study of biology relevant to human physiology and health. It is therefore important to have the power of large-scale genetic analysis available for the study of a mammalian species that can aid in the study of human disease. Given that the entire human genome is presently being sequenced, the comprehensive genetic analysis of a related mammalian species will provide a means to determine the function of genes cloned from the human genome. At present, rodents, and particularly mice, provide the best model for genetic manipulation and analysis of mammalian physiology.

Gene trapping has been used as an analytical tool to identify genes and regulatory regions in a variety of animal cell types. One system that has proved particularly useful is based on the use of ROSA (reverse orientation splice acceptor) retroviral vectors (Friedrich and Soriano, 1991 and 1993).

The ROSA system can generate mutations that result in a detectable homozygous phenotype with a high frequency. About 50% of all the insertions caused embryonic lethality. The specifically mutated genes may easily be cloned since the gene trapping event produces a fusion transcript. This fusion transcript has trapped exon sequences appended to the sequences of the selectable marker allowing the latter to be used as a tag in polymerase chain reaction (PCR)-based protocols, or by simple cDNA cloning. Examples of genes isolated by these methods include a transcription factor related to human TEF-1 (transcription enhancer factor-1) which is required in the development of the heart (Chen et al., 1994, Genes Devel. 8:2293–2301. Another (spock), is distantly related to yeast genes encoding secretion proteins and is important during gastrulation.

The above experiments have established that the ROSA system is an effective analytical tool for genetic analysis in mammals. However, the structure of many ROSA vectors selects for the "trapping" of 5' exons which, in many cases, do not encode proteins. Such a result is adequate where one wishes to identify and eventually clone control (i.e., promoter or enhancer) sequences, but is not optimal where the generation of insertion-inactivated null mutations is desired, and relevant coding sequence is needed. Thus, the construction of large-scale mutant (preferably null mutant) libraries requires the use of vectors that have been designed to select for insertion events that have occurred within the coding region of the mutated genes as well as vectors that are not limited to detecting insertions into expressed genes.

3.0 SUMMARY OF THE INVENTION

An object of the present invention is to provide a set of genetically altered cells (the 'Library'). The genetic alterations are of sufficient randomness and frequency such that the combined population of cells in the Library represent mutations in essentially every gene found in the cell's genome. The Library is used as a source for obtaining specifically mutated cells, cell lines derived from the individually mutated cells, and cells for use in the production of transgenic non-human animals.

A further object is to provide the vectors, both DNA and retroviral based, that may be used to generate the Library. Typically, at least two distinct vector designs will be used in order to mutate genes that are actively expressed in the target cell, and genes that are not expressed in the target cell. Combining the mutant cells obtained using both types of vectors best ensures that the Library provides a comprehensive set of gene mutations.

One vector contemplated by the present invention is designed to replace the normal 3' end of an animal cell transcript with a foreign exon. Such a vector shall generally be engineered to comprise a selectable marker, a splice acceptor site operatively positioned upstream (5') from the initiation codon of the selectable marker, and a polyadenylation site operatively positioned downstream (3') from the termination codon (3' end) of the selectable marker. Preferably, the vector will not comprise a promoter element operatively positioned upstream from the coding region of the selectable marker, and will not comprise a splice donor sequence operatively positioned between the 3' end of the coding region of the selectable marker and the polyadenylation site.

An additional vector contemplated by the present invention is a vector designed to insert foreign exons internal to animal cell transcripts (i.e., the foreign exon is flanked on both sides by endogenous exons). Such a vector shall generally comprise a selectable marker, a splice acceptor site operatively positioned 5' to the initiation codon of the selectable marker, a splice donor site operatively positioned 3' to said selectable marker, and a sequence comprising a nested set of stop codons in each of the three reading frames located between the end of said selectable marker and said splice donor site. Preferably, this vector shall not comprise a polyadenylation site operatively positioned 3' to the coding region of said selectable marker, and shall not comprise a promoter element operatively positioned 5' to the coding region of said selectable marker.

Yet another class of vector contemplated by the present invention is a vector for inserting foreign exons into animal cell transcripts that comprises a selectable marker, a promoter element operatively positioned 5' to the selectable marker, a splice donor site operatively positioned 3' to the selectable marker, and a second exon located upstream from the promoter element that disrupts the splicing or readthrough expression of the transcript produced by the promoter element. Typically, the second exon may comprise, in operative combination, splice acceptor and splice donor sequences. Optionally, a polyadenylation site may be incorporated in addition to or in lieu of the splice donor sequence. The second exon may also incorporate a nested set of stop codons in each of the three reading frames. Preferably, such a vector shall not comprise a transcription terminator or polyadenylation site operatively positioned relative to the coding region of the selectable marker, and shall not comprise a splice acceptor site operatively positioned between the promoter element and the initiation codon of said selectable marker.

Accordingly, an embodiment of the present invention is a library of genetically altered cells that have been treated to stably incorporate one or more types of the vectors described above.

Accordingly, the presently described library of cultured animal cells may be made by a process comprising the steps of treating (i.e., infecting or transfecting) a population of cells to stably integrate a vector that mediates the splicing of a foreign exon internal to a cellular transcript, transfecting another population of cells to stably integrate a vector that mediates the splicing of a foreign exon 5' to an exon of a cellular transcript, and selecting for transduced cells that express the products encoded by the foreign exons.

Alternatively, an additional embodiment of the present invention describes a mammalian cell library made by a method comprising the steps of: transfecting a population of cells with a vector capable of expressing a selectable marker in the cell only after the vector inserts into the host genome; transfecting or infecting a population of cells with a vector containing a selectable marker that is substantially only expressed by cellular control sequences (after the vector integrates into the host cells genome); and growing the transfected cells under conditions that select for the expression of the selectable marker.

In an additional embodiment of the present invention, the two populations of transfected cells will be individually grown under selective conditions, and the resulting mutated population of cells collectively comprises a substantially comprehensive library of mutated cells.

In an additional embodiment of the present invention, the individual mutant cells in the library are separated and clonally expanded. Additionally, the clonally expanded mutant cells may then be analyzed to ascertain the DNA sequence, or partial DNA sequence of the mutated host gene.

The presently described methods of making, organizing, and indexing libraries of mutated animal cells are also broadly applicable to virtually any eukaryotic cells that may be genetically manipulated and grown in culture.

The invention provides for sequencing every gene mutated in the Library. The resulting sequence database subsequently serves as an index for the library. In essence, every cell line in the Library is individually catalogued using the partial sequence information. The resulting sequence is specific for the mutated gene since the present methods are designed to obtain sequence information from exons that have been spliced to the marker sequence. Since the coverage of the mutagenesis is preferably the entire set of genes in the genome, the resulting Library sequence database contains sequence from essentially every gene in the cell. From this database, a gene of interest can be identified. Once identified, the corresponding mutant cell may be withdrawn from the Library based on cross reference to the sequence data.

An additional embodiment of the invention provides for methods of isolating mutations of interest from the Library. Two methods are proposed for obtaining individual mutant cell lines from the Library. The first provides a scheme where clones of the cells generated using the above vectors are pooled into sets of defined size. Using the procedure described below which utilizes reverse transcription (RT) and polymerase chain reaction (PCR), a cell line with a mutation in a gene whose sequence is partly or wholly known is isolated from organized sets of these pools. A few rounds of this screening procedure results in the isolation of the desired individual cell line.

A second procedure involves the sequencing of regions flanking the vector insertion sites in the various cells in the library. The sequence database generated from these data effectively constitutes an index of the clones in the library that may be used to identify cells having mutations in specific genes.

4.0 DESCRIPTION OF THE FIGURES

FIG. 1. Shows a diagrammatic representation of 5 different vectors that are generally representative of the type of vectors that may be used in the present invention.

Figure 2:
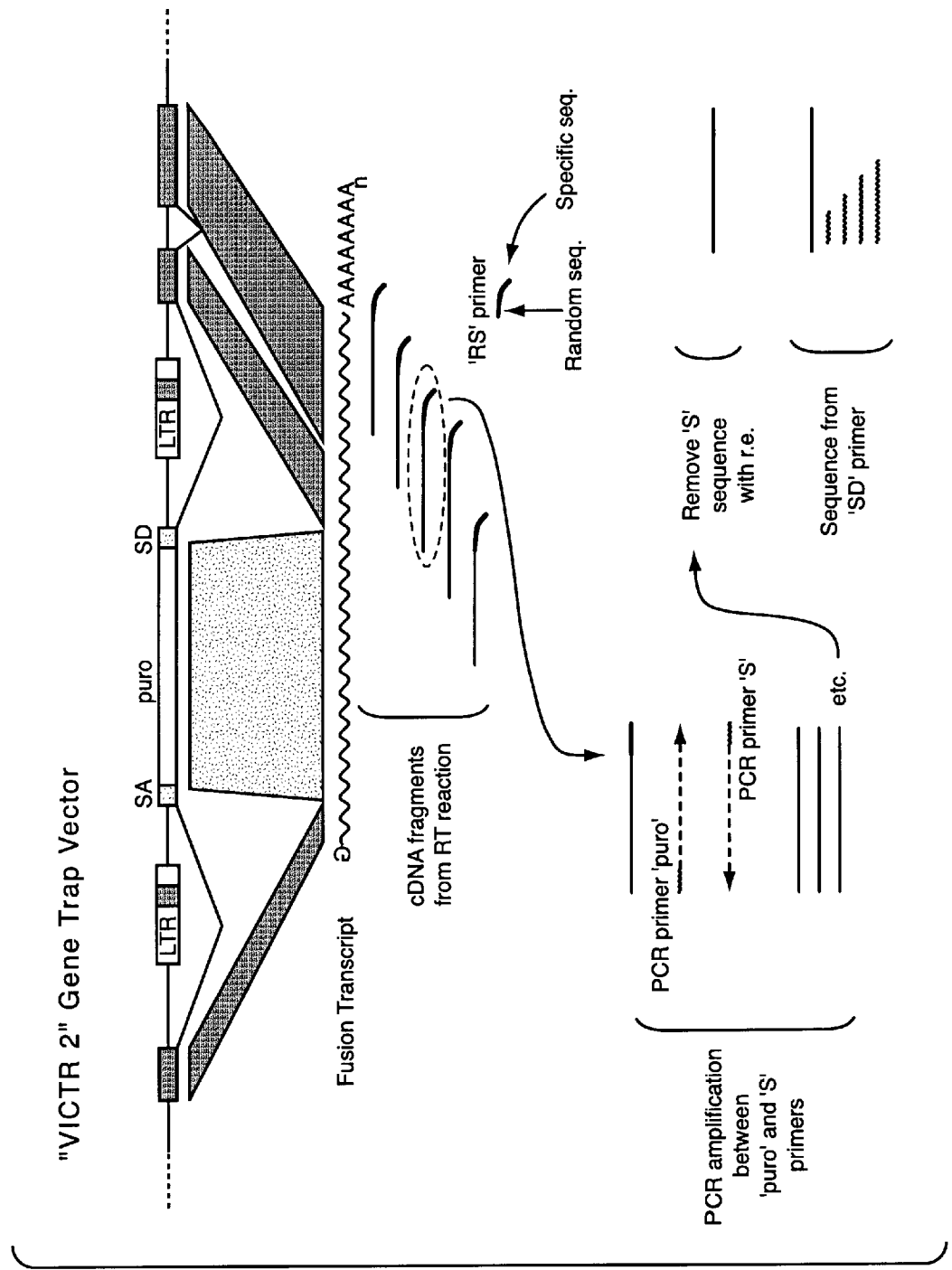

FIG. 2. Shows a general strategy for identifying "trapped" cellular sequences by PCR analysis of the cellular exons that flank the foreign intron introduced by the VICTR 2 vector.

Figure 3:
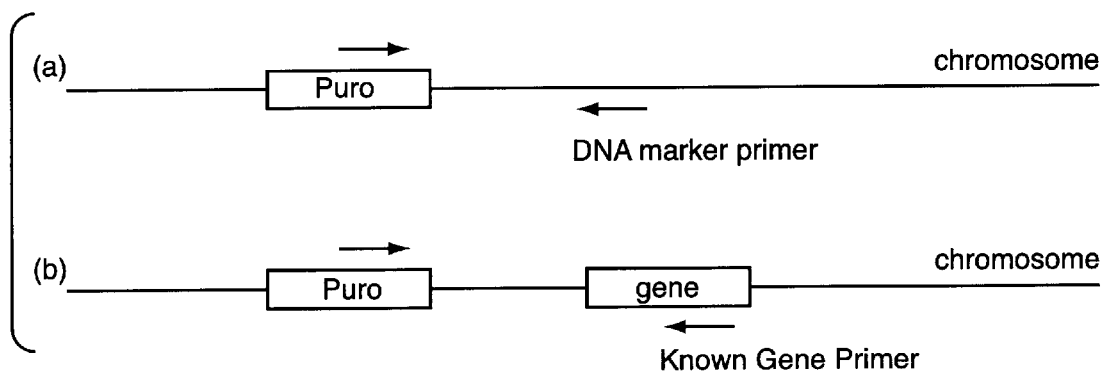

FIG. 3 shows a PCR based strategy for identifying tagged genes by chromosomal location.

Figure 4:
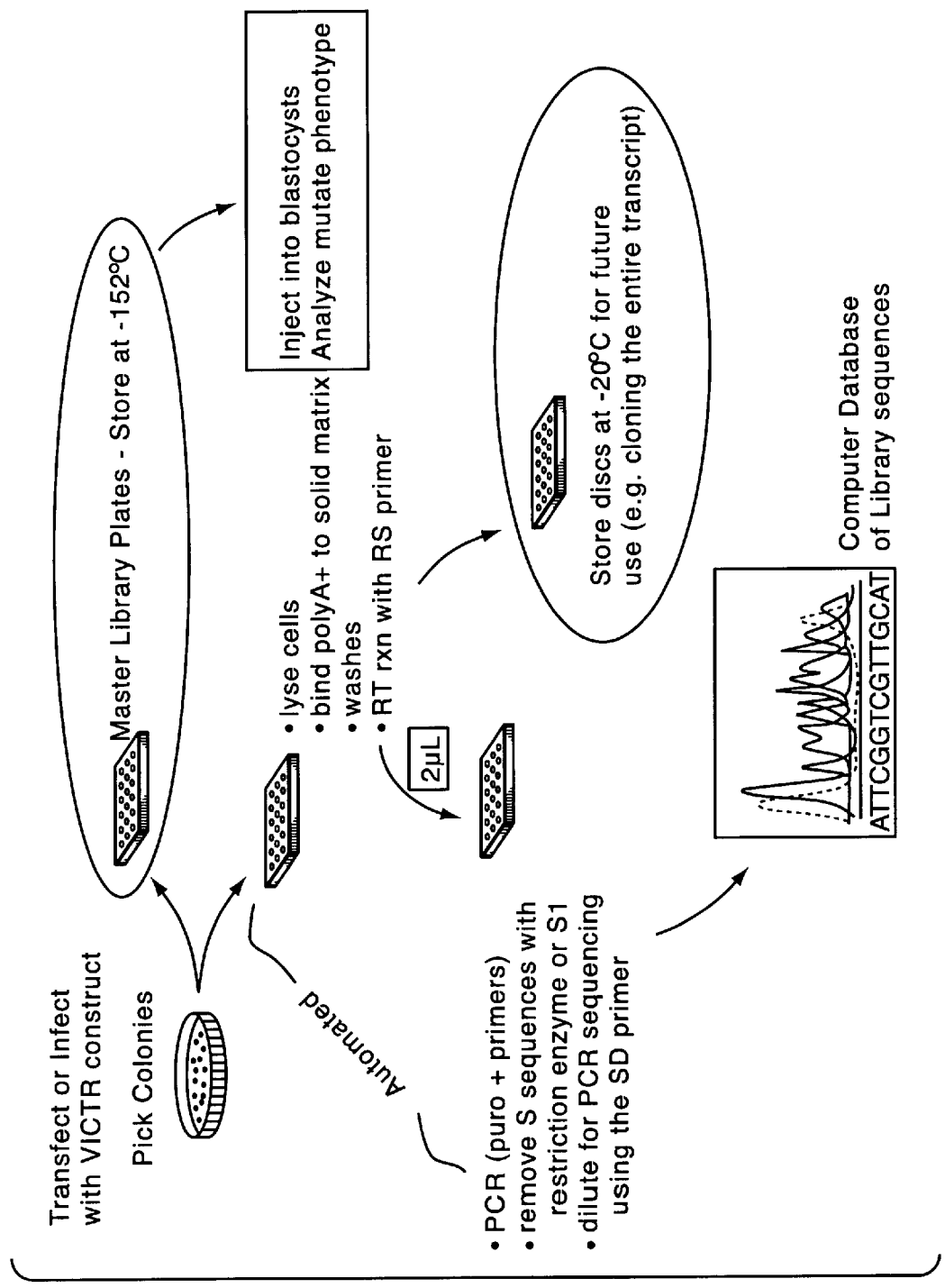

FIG. 4. Is a diagrammatic representation of a strategy of identifying or indexing the specific clones in the library via PCR analysis and sequencing of mRNA samples obtained from the cells in the library.

FIG. 5. Is a diagrammatic representation of a method of isolating positive clones by screening pooled mutant cell clones.

FIG. 6. Partial nucleic acid or predicted amino acid sequence data from 9 clones (SEQ ID NOS:1–18) (OST1-9) isolated using the described techniques aligned with similar sequences from previously characterized genes.

5.0 DETAILED DESCRIPTION OF THE INVENTION

The present invention describes a novel indexed library containing a substantially comprehensive set of mutations in the host cell genome, and methods of making and using the same. The presently described Library comprises as a set of cell clones that each possess at least one mutation (and preferably a single mutation) caused by the insertion of DNA that is foreign to the cell. The particularly novel features of the Library include the methods of construction, and indexing. To index the library, the mutant cells of the library are clonally expanded and each mutated gene is at least partially sequenced. The Library thus provides a novel tool for assessing the specific function of a given gene. The insertions cause a mutation which allow for essentially every gene represented in the Library to be studied using genetic techniques either in vitro or in vivo (via the generation of transgenic animals). For the purposes of the present invention, the term "essentially every gene" shall refer to the statistical situation where there is generally at least about a 70 percent probability that the genomes of cells used to construct the library collectively contain at least one inserted vector sequence in each gene, preferably a 85 percent probability, and more specifically at least about a 95 percent probability as determined by a standard Poisson distribution.

Also for the purposes of the present invention the term "gene" shall refer to any and all discrete coding regions of the cell's genome, as well as associated noncoding and regulatory regions. Additionally, the term operatively positioned shall refer to the control elements or genes that are provided with the proper orientation and spacing to provide the desired or indicated functions of the control elements or genes.

For the purposes of the present invention, a gene is "expressed" when a control element in the cell mediates the production of functional or detectable levels of mRNA encoded by the gene, or a selectable marker inserted therein. A gene is not expressed where the control element in the cell is absent, has been inactivated, or does not mediate the production of functional or detectable levels of mRNA encoded by the gene, or a selectable marker inserted therein.

5.1 Vectors Used to Build the Library

A number of investigators have developed gene trapping vectors and procedures for use in mouse and other cells (Allen et al., 1988; Bellen et al., 1989, Genes Dev. 3(9):1288–1300; Bier et al., 1989, Genes Dev. 3(9):1273–1287; Bonnerot et al., 1992, J Virol. 66(8):4982–4991; Brenner et al., 1989; Chang et al., 1993; Friedrich and Soriano, 1993; Friedrich and Soriano, 1991; Goff, 1987, Methods Enzymol. 152:469–481; Gossler et al.; Hope, 1991; Kerr et al., 1989; Reddy et al., 1991; Reddy et al., 1992; Skarnes et al., 1992; von Melchner and Ruley; Yoshida et al., 1995). The gene trapping system described in the present invention is based on significant improvements to the published SA (splice acceptor) DNA vectors and the ROSA (reverse orientation, splice acceptor) retroviral vectors (Chen et al., 1994; Friedrich and Soriano, 1991 and 1993). The presently described vectors also use a selectable marker called βgeo. This gene encodes a protein which is a fusion between the β-galactosidase and neomycin phosphotransferase proteins. The presently described vectors place a splice acceptor sequence upstream from the βgeo gene and a polyadenylation signal sequence downstream from the marker. The marker is integrated after transfection by, for example, electroporation (DNA vectors), or retroviral infection, and gene trap events are selected based on resistance to G418 resulting from activation of βgeo expression by splicing from the endogenous gene into the ROSA splice acceptor. This type of integration disrupts the transcription unit and preferably results in a null mutation at the locus.

Although gene trapping has proven a useful analytical tool, the present invention contemplates gene trapping on a large scale. The vectors utilized in the present invention have been engineered to overcome the shortcomings of the early gene trap vector designs, and to facilitate procedures allowing high throughput. In addition, procedures are described that allow the rapid and facile acquisition of sequence information from each trapped cDNA which may be adapted to allow complete automation. These latter procedures are also designed for flexibility so that additional molecular information can easily be obtained subsequently. The present invention therefore incorporates gene trapping into a larger and unique tool. A specially organized set of gene trap clones that provide a novel and powerful new tool of genetic analysis.

The presently described vectors are superficially similar to the ROSA family of vectors, but constitute significant improvements and provide for additional features that are useful in the construction and indexing of the Library. Typically, gene trapping vectors are designed to detect insertions into transcribed gene regions within the genome. They generally consist of a selectable marker whose normal expression is handicapped by exclusion of some element required for proper transcription. When the vector integrates into the genome, and acquires the necessary element by juxtaposition, expression of the selectable marker is activated. When such activation occurs, the cell can survive when grown in the appropriate selective medium which allows for the subsequent isolation and characterization of the trapped gene. Integration of the gene trap generally causes the gene at the site of integration to be mutated.

Some gene trapping vectors have a splice acceptor preceding a selectable marker and a poly-adenylation signal following the selectable marker, and the selectable marker gene has its own initiator ATG codon. Using this arrangement, the fusion transcripts produced after integration generally only comprise exons 5' to the insertion site to the known marker sequences. Where the vector has inserted into the 5' region of the gene, it is often the case that the only exon 5' to the vector is a non-coding exon. Accordingly, the sequences obtained from such fusions do not provide the desired sequence information about the relevant gene products. This is because untranslated sequences are generally less well conserved than coding sequences.

To compensate for the short-comings of earlier vectors, the vectors of the present invention have been designed so that 3' exons are appended to the fusion transcript by replacing the poly-adenylation and transcription termination signals of earlier ROSA vectors with a splice donor (SD) sequence. Consequently transcription and splicing generally results in a fusion between all or most of the endogenous transcript and the selectable marker exon, for example βgeo, neomycin (neo) or puromycin (puro). The exon sequences immediately 3' to the selectable marker exon may then be sequenced and used to establish a database of expressed sequence tags. The presently described procedures will typically provide approximately 200 nucleotides of sequence, or more. These sequences will generally be coding and therefore informative. The prediction that the sequence obtained will be from coding region is based on two factors. First, gene trap vectors are generally found near the 5' end of the gene immediately after untranslated exons because the method selects for integration events that place the initiator ATG of the selectable marker as the first encountered, and thus used, for translation. Second, mammalian transcripts have short 5' untranslated regions (UTRs) which are typically between 50 and 150 nucleotides in length.

The obtained sequence information also provides a ready source of probes that may be used to isolate the full-length gene or cDNA from the host cell, or as heterologous probes for the isolation of homologous genes in other species.

Internal exons in mammalian transcripts are generally quite small, on the average 137 bases with few over 300 bases. Consequently, a large internal exon may be spliced less efficiently. Thus, the presently described vectors have been designed to sandwich relatively small selectable markers (for example: neo ,~800 bases, or a smaller drug resistance gene such as puro ,~600 bases) between the requisite splicing elements to produce relatively small exons. Exons of this size are more typical of mammalian exons and do not present undue problems for the splicing machinery of the cell. Such a design consideration is novel to the presently disclosed gene trapping vectors. Accordingly, an additional embodiment of the claimed vectors is that the respective splice acceptor and splice donor sites are engineered such that they are operatively positioned close to the ends of the selectable marker coding region (the region spanning from the initiation codon to the termination codon). Generally, the splice acceptor or splice donor sequences shall appear within about 80 bases from the nearest end of the selectable marker coding region, preferably within about 50 bases from the nearest end of the coding region, more preferably within about 30 bases from the nearest end of the coding regions and specifically within about 20 bases of the nearest end of the selectable marker coding region.

The new vectors are represented in retroviral form in FIG. 1. They are used by infecting target cells with retroviral particles such that the proviruses shown in the schematic can be found in the genome of the target. These vectors are called VICTR which is an acronym for "viral constructs for trapping".

The presently described retroviral vectors may be used in conjunction with retroviral packaging cell lines such as those described in U.S. Pat. No. 5,449,614 ("'614 patent") issued Sep. 12, 1995, herein incorporated by reference. Where non-mouse animal cells are to be used as targets for generating the described libraries, packaging cells producing retrovirus with amphotropic envelopes will generally be employed to allow infection of the host cells.

The mutagenic gene trap DNA may also be introduced into the target cell genome by various transfection techniques which are familiar to those skilled in the art such as electroporation, lipofection, or calcium phosphate precipitation. Examples of such techniques may be found in Sambrook et al. (1989) *Molecular Cloning* Vols. I–III, Cold Spring Harbor Laboratory Press, Cold Spring Harbor, N.Y., and *Current Protocols in Molecular Biology* (1989) John Wiley & Sons, all Vols. and periodic updates thereof, herein incorporated by reference. The transfected versions of the retroviral vectors are typically plasmid DNA molecules containing DNA cassettes comprising the described features between the retroviral LTRs.

The vectors VICTR 1 and 2 (FIG. 1) are designed to trap genes that are transcribed in the target cell. To trap genes that are not expressed in the target cell, gene trap vectors such as VICTR 3, 4 and 5 (described below) are provided. These vectors have been engineered to contain a promoter element capable of initiating transcription in virtually any cell type which is used to transcribe the coding sequence of the selectable marker. However, in order to get proper translation of the marker product, and thus render the cell resistant to the selective antibiotic, a polyadenylation signal and a transcription termination sequence must be provided. Vectors VICTR 3 through 5 are constructed such that an effective polyadenylation signal can only be provided by splicing with an externally provided downstream exon that contains a poly-adenylation site. Therefore, since the selectable marker coding region ends only in a splice donor sequence, these vectors must be integrated into a gene in order to be properly expressed. In essence, these vectors append the foreign exon encoding the marker to the 5' end of an endogenous transcript. These events will tag genes and create mutations that are used to make clones that will become part of the Library.

With the above design considerations, the VICTR series of vectors, or similarly designed and constructed vectors, have the following features. VICTR 1 is a terminal exon gene trap. VICTR 1 does not contain a control region that effectively mediates the expression of the selectable marker gene. Instead, the coding region of the selectable marker contained in VICTR 1, in this case encoding puromycin resistance (but which can be any selectable marker functional in the target cell type), is preceded by a splice acceptor sequence and followed by a polyadenylation addition signal sequence. The coding region of the puro gene has an initiator ATG which is downstream and adjacent to a region of sequence that is most favorable for translation initiation in eukaryotic cells—the so called Kozak consensus sequence (Kozak, 1989, J. Cell, Biol. 108(2):229–241). With a Kozak sequence and an initiator ATG, the puro gene in VICTR 1 is activated by integrating into the intron of an active gene, and the resulting fusion transcript is translated beginning at the puromycin initiation (ATG/AUG) codon. However, terminal gene trap vectors need not incorporate an initiator ATG codon. In such cases, the gene trap event requires splicing and the translation of a fusion protein that is functional for the selectable marker activity. The inserted puromycin coding sequence must therefore be translated in the same frame as the "trapped" gene.

The splice acceptor sequence used in VICTR 1 and other members of the VICTR series is derived from the adenovirus major late transcript splice site located at the intron 1/exon 2 boundary. This sequence contains a polypyrimidine stretch preceding the AG dinucleotide which denotes the actual splice site. The presently described vectors contemplate the use of any similarly derived splice acceptor sequence. Preferably, the splice acceptor site will only rarely, if ever, be involved in alternative splicing events.

The polyadenylation signal at the end of the puro gene is derived from the bovine growth hormone gene. Any similarly derived polyadenylation signal sequence could be used if it contains the canonical AATAAA and can be demonstrated to terminate transcription and cause a polyadenylate tail to be added to the engineered coding exons.

VICTR 2 is a modification of VICTR 1 in which the polyadenylation signal sequence is removed and replaced by a splice donor sequence. Like VICTR 1, VICTR 2 does not contain a control region that effectively mediates the expression of the selectable marker gene. Typically, the splice donor sequence to be employed in a VICTR series vector shall be determined by reference to established literature or by experimentation to identify which sequences properly initiate splicing at the 5' end of introns in the desired target cell. The specifically exemplified sequence, AGGTAAGT, results in splicing occurring in between the two G bases. Genes trapped by VICTR 2 splice upstream exons onto the puro exon and downstream exons onto the end of the puro exon. Accordingly, VICTR 2 effectively mutates gene expression by inserting a foreign exon in-between two naturally occurring exons in a given transcript. Again, the puro gene may or may not contain a consensus Kozak translation initiation sequence and properly positioned ATG initiation codon.

As discussed above, gene trapping by VICTR 1 and VICTR 2 requires that the mutated gene is expressed in the target cell line. By incorporating a splice donor into the VICTR traps, transcript sequences downstream from the gene trap insertion can be determined. As described above, these sequences are generally more informative about the gene mutated since they are more likely to be coding sequences. This sequence information is gathered according to the procedures described below.

VICTR 3, VICTR 4 and VICTR 5 are gene trap vectors that do not require the cellular expression of the endogenous trapped gene. The VICTR vectors 3 through 5 all comprise a promoter element that ensures that transcription of the selectable marker would be found in all cells that have taken up the gene trap DNA. This transcription initiates from a promoter, in this case the promoter element from the mouse phosphoglycerate kinase (PGK) gene. However, since the constructs lack a polyadenylation signal there can be no proper processing of the transcript and therefore no translation. The only means to translate the selectable marker and get a resistant cell clone is by acquiring a polyadenylation signal. Since polyadenylation is known to be concomitant with splicing, a splice donor is provided at the end of the selectable marker. Therefore, the only positive gene trap events using VICTR 3 through 5 will be those that integrate into a gene's intron such that the marker exon is spliced to downstream exons that are properly polyadenylated. Thus genes mutated with the VICTR vectors 3 through 5 need not be expressed in the target cell, and these gene trap vectors can mutate all genes having at least one intron. The design of VICTR vectors 3 through 5 requires a promoter element that will be active in the target cell type, a selectable marker and a splice donor sequence. Although a specific promoter was used in the specific embodiments, it should be understood that appropriate promoters may be selected that are known to be active in a given cell type. Typically, the considerations for selecting the splice donor sequence are identical to those discussed for VICTR 2, supra.

VICTR 4 differs from VICTR 3 only by the addition of a small exon upstream from the promoter element of VICTR 4. This exon is intended to stop normal splicing of the mutated gene. It is possible that insertion of VICTR 3 into an intron might not be mutagenic if the gene can still splice between exons, bypassing the gene trap insertion. The exon in VICTR 4 is constructed from the adenovirus splice acceptor described above and the synthetic splice donor also described above. Stop codons are placed in all three reading frames in the exon, which is about 100 bases long. The stops would truncate the endogenous protein and presumably cause a mutation.

A conceptually similar alternative design uses a terminal exon like that engineered into VICTR 5. Instead of a splice donor, a polyadenylation site is used to terminate transcription and produce a truncated message. Stops in all three frames are also provided to truncate the endogenous protein as well as the resulting transcript.

All of the traps of the VICTR series are designed such that a fusion transcript is formed with the trapped gene. For all but VICTR 1, the fusion contains cellular exons that are located 3' to the gene trap insertion. All of the flanking exons may be sequenced according to the methods described in the following section. To facilitate sequencing, specific sequences are engineered onto the ends of the selectable marker (e.g., puromycin coding region). Examples of such sequences include, but are not limited to unique sequences for priming PCR, and sequences complementary to the standard M13 forward sequencing primer. Additionally, stop codons are added in all three reading frames to ensure that no anomalous fusion proteins are produced. All of the unique 3' primer sequences are followed immediately by the synthetic 9 base pair splice donor sequence. This keeps the size of the exon comprising the selectable marker (puro gene) at a minimum to best ensure proper splicing, and positions the amplification and sequencing primers immediately adjacent to the flanking "trapped" exons to be sequenced as part of the construction of a Library database.

When any members of the VICTR series are constructed as retroviruses, the direction of transcription of the selectable marker is opposite to that of the direction of the normal transcription of the retrovirus. The reason for this organization is that the transcription elements such as the polyadenylation signal, the splice sites and the promoter elements found in the various members of the VICTR series interfere with the proper transcription of the retroviral genome in the packaging cell line. This would eliminate or significantly reduce retroviral titers. The LTRs used in the construction of the packaging cell line are self-inactivating. That is, the enhancer element is removed from the 3' U3 sequences such that the proviruses resulting from infection would not have an enhancer in either LTR. An enhancer in the provirus may otherwise affect transcription of the mutated gene or nearby genes.

Since a 'cryptic' splice donor sequence is found in the inverted LTRs, this splice donor sequence has been removed from the VICTR vectors by site specific mutagenesis. It was deemed necessary to remove this splice donor so that it would not affect the trapping splicing events.

Although specific gene trapping vectors have been discussed at length above, the invention is by no means to be limited to such vectors. Several different types of vectors that may also be used to incorporate relatively small engineered exons into a target cell transcripts include, but are not limited to, adenoviral vectors, adenoassociated virus vectors, SV40 based vectors, and papilloma virus vectors. Additionally, DNA vectors may be directly transferred into the target cells using any of a variety of chemical or physical means such as lipofection, chemical transfection, electroporation, and the like.

Although, the use of specific selectable markers have been disclosed and discussed herein, the present invention is in no way limited to the specifically disclosed markers. Additional markers (and associated antibiotics) that are suitable for either positive or negative selection of eukaryotic cells are disclosed, inter alia, in Sambrook et al. (1989) *Molecular Cloning* Vols. I–III, Cold Spring Harbor Laboratory Press, Cold Spring Harbor, N.Y., and *Current Protocols in Molecular Biology* (1989) John Wiley & Sons, all Vols. and periodic updates thereof, as well as Table I of U.S. Pat. No. 5,464,764 issued Nov. 7, 1995, the entirety of which is herein incorporated by reference. Any of the disclosed markers, as well as others known in the art, may be used to practice the present invention.

5.2. The Analysis of Mutated Genes and Transcripts

The presently described invention allows for large-scale genetic analysis of the genomes of any organism for which there exists cultured cell lines. The Library may be constructed from any type of cell that can be transfected by standard techniques or infected with recombinant retroviral vectors.

Where mouse ES cells are used, then the Library becomes a genetic tool able to completely represent mutations in essentially every gene of the mouse genome. Since ES cells can be injected back into a blastocyst and become incorporated into normal development and ultimately the germ line, the cells of the Library effectively represent a complete panel of mutant transgenic mouse strains (see generally, U.S. Pat. No. 5,464,764 issued Nov. 7, 1995, herein incorporated by reference).

Similar methods are deemed to enable the construction of virtually any non-human transgenic animal (or animal capable of being rendered transgenic). Such nonhuman transgenic animals may include, for example, transgenic pigs, transgenic rats, transgenic rabbits, transgenic cattle, transgenic goats, and other transgenic animal species, particularly mammalian species, known in the art. Additionally, bovine, ovine, and porcine species, other members of the rodent family, e.g. rat, as well as rabbit and guinea pig and non-human primates, such as chimpanzee, may be used to practice the present invention.

Transgenic animals produced using the presently described library and/or vectors are useful for the study of basic biological processes and diseases including, but not limited to, aging, cancer, autoimmune disease, immune disorders, alopecia, glandular disorders, inflammatory disorders, diabetes, arthritis, high blood pressure, atherosclerosis, cardiovascular disease, pulmonary disease, degenerative diseases of the neural or skeletal systems, Alzheimer's disease, Parkinson's disease, asthma, developmental disorders or abnormalities, infertility, epithelial ulcerations, and microbial pathogenesis (a relatively comprehensive review of such pathogens is provided, inter alia, in Mandell et al., 1990, "Principles and Practice of Infectious Disease" 3rd. ed., Churchill Livingstone Inc., New York, N.Y. 10036, herein incorporated by reference).

5.2.1. Constructing a Library of Individually Mutated Cell Clones

The vectors described in the previous section are used to infect (or transfect) cells in culture, for example, mouse embryonic stem (ES) cells. Those insertions for which a gene is trapped as described are identified by being resistant to the antibiotic (e.g., puromycin) which has been added to the culture. Individual clones (colonies) are moved from a culture dish to individual wells of a multi-welled tissue culture plate (e.g. one with 96 wells). From this platform, the clones may be duplicated for storage and subsequent analysis. Each multi-well plate of clones is then processed by molecular biological techniques described in the following section in order to derive sequence of the gene that has been mutated. This entire process is presented schematically in FIG. 4 (described below).

5.2.2. Identifying and Sequencing the Tagged Genes in the Library

The relevant nucleic acid (and derived amino acid sequence information) will be obtained using PCR-based techniques that rely on knowing part of the sequence of the fusion transcripts (see generally, Frohman et al., 1988, Proc. Natl. Acad. Sci. U.S.A. 85(23):8998–9000, and U.S. Pat. Nos. 4,683,195 to Saiki et al., and 4,683,202 to Mullis, which are herein incorporated by reference). Typically, such sequence shall be encoded by the foreign exon containing the selectable marker. The procedure is represented schematically in FIG. 2. Although each step of the procedure may be done manually, the procedure is also designed to be carried out using robots that can deliver reagents to multi well culture plates (e.g., but not limited to, 96-well plates)

The first step generates single stranded complementary DNA which is used in the PCR amplification reaction (FIG. 2). The RNA substrate for cDNA synthesis may either be total cellular RNA or an mRNA fraction; preferably the latter. mRNA is isolated from cells directly in the wells of the tissue culture dish. The cells are lysed and mRNA is bound by the complementary binding of the poly-adenylate tail to a solid matrix-bound poly-thymidine. The bound mRNA is washed several times and the reagents for the reverse transcription (RT) reaction are added. cDNA synthesis in the RT reaction is initiated at random positions along the message by the binding of a random sequence primer (RS). This RS primer will have 6–9 random nucleotides at the 3' end to bind sites in the mRNA to prime cDNA synthesis, and a 5' tail sequence of known composition to act as an anchor for PCR amplification in the next step. There is therefore no specificity for the trapped message in the RT step. Alternatively, a poly-dT primer appended with the specific sequences for the PCR may be used. Synthesis of the first strand cDNA would then initiate at the end of each trapped gene. At this point in the procedure, the bound mRNA may be stored (at between about −70° C. and about 4° C.) and reused multiple times. Such storage is a valuable feature where one subsequently desires to analyze individual clones in more detail. The bound mRNA may also be used to clone the entire transcript by PCR-based protocols.

Specificity for the trapped, fusion transcript is introduced in the next step, PCR amplification. The primers for this reaction are complementary to the anchor sequence of the RS primer and to the selectable marker. Double stranded fragments between a fixed point in the selectable marker gene and various points downstream in the appended transcript sequence are amplified. It is these fragments which will become the substrates for the sequencing reaction. The various end-points along the transcript sequence are determined by the binding of the random primer during the RT reaction. These PCR products are diluted into the sequencing reaction mix, denatured and sequenced using a primer specific for the splice donor sequences of the gene trap exon. Although, standard radioactively labeled nucleotides may be used in the sequencing reactions, sequences will typically be determined using standard dye terminator sequencing in conjunction with automated sequencers (e.g., ABI sequencers and the like).

Several fragments of various sizes may serve as substrates for the sequencing reactions. This is not a problem since the sequencing reaction proceeds from a fixed point as defined by a specific primer sequence. Typically, approximately 200 nucleotides of sequence are obtained for each trapped transcript. For the PCR fragments that are shorter than this, the sequencing reaction simply 'falls off' the end. Sequences further 3' are then covered by the longer fragments amplified during PCR. One problem is the anchor sequences 'S' derived from the RS primer. When these are encountered during sequencing of smaller fragments, they register as anomalous dye signals on the sequencing gels. To circumvent this potential problem, a restriction enzyme recognition site is included in the S sequence. Digestion of the double stranded PCR products with this enzyme prior to sequencing eliminates the heterologous S sequences.

5.2.3. Identifying the Tagged Genes by Chromosomal Location

Any individually tagged gene may also be identified by PCR using chromosomal DNA as the template. To find an individual clone of interest in the Library arrayed as described above, genomic DNA is isolated from the pooled clones of ES cells as presented in FIG. 3. One primer for the PCR is anchored in the gene trap vector, e.g., a puro exon-specific oligonucleotide. The other primer is located in the genomic DNA of interest. This genomic DNA primer may consist of either (1) DNA sequence that corresponds to the coding region of the gene of interest, or (2) DNA sequence from the locus of the gene of interest. In the first case, the only way that the two primers used may be juxtaposed to give a positive PCR results (e.g., the correct size double-stranded DNA product) is if the gene trap vector has inserted into the gene of interest. Additionally, degenerate primers may be used, to identify and isolate related genes of interest. In the second case, the only way that the two primers used may be juxtaposed to provide the desired PCR result is if the gene trap vector has inserted into the region of interest that contains the primer for the known marker.

For example, if one wishes to obtain ES cell clones from the library that contain mutated genes located in a certain chromosomal position, PCR primers are designed that correspond to the puro gene (the puro-anchored primer) and a primer that corresponds to a marker known to be located in the region of interest. Several different combinations of marker primers and primers that are located in the region of interest may also be used to obtain optimum results. In this manner, the mutated genes are identified by virtue of their location relative to sets of known markers. Genes in a particular chromosomal region of interest could therefore be identified. The marker primers could also be designed correspond to sequences of known genes in order to screen for mutations in particular genes by PCR on genomic DNA templates. While this method is likely to be less informative than the RT-PCR strategy described below, this technique would be useful as a alternative strategy to identify mutations in known genes. In addition, primers that correspond to sequence of known genes could be used in PCR reactions with marker-specific primers in order to identify ES cell clones that contain mutations in genes proximal to the known genes. The sensitivity of detection is adequate to find such events when positive clones are subsequently identified as described below in the RT-PCR strategy.

5.3. A Sequence Database Identifies Genes Mutated in the Library

Using the procedures described above, approximately 200 to about 600 bases of sequence from the cellular exons appended to the selectable marker exon (e.g., puro exon in VICTR vectors) may be identified. These sequences provide a means to identify and catalogue the genes mutated in each clone of the Library. Such a database provides both an index for the presently disclosed libraries, and a resource for discovering novel genes. Alternatively, various comparisons can be made between the Library database sequences and any other sequence database as would be familiar to those practiced in the art.

The novel utility of the Library lies in the ability for a person to search the Library database for a gene of interest based upon some knowledge of the nucleic acid or amino acid sequence. Once a sequence is identified, the specific clone in the Library can be accessed and used to study gene function. This is accomplished by studying the effects of the mutation both in vitro and in vivo. For example, cell culture systems and animal models (i.e., transgenic animals) may be directly generated from the cells found in the Library as will be familiar to those practiced in the art.

Additionally, the sequence information may be used to generate a highly specific probe for isolating both genomic clones from existing data bases, as well as a full length cDNA. Additionally, the probe may be used to isolate the homologous gene from sufficiently related species, including humans. Once isolated, the gene may be over expressed, or used to generate a targeted knock-out vector that may be used to generate cells and animals that are homozygous for the mutation of interest. Such animals and cells are deemed to be particularly useful as disease models (i.e., cancer, genetic abnormalities, AIDS, etc.), for developmental study, to assay for toxin susceptibility or the efficacy of therapeutic agents, and as hosts for gene delivery and therapy experiments (e.g., experiments designed to correct a specific genetic defect in vivo).

5.4. Accessing Clones in the Library by a Pooling and Screening Procedure

An alternative method of accessing individual clones is by searching the Library database for sequences in order to isolate a clone of interest from pools of library clones. The Library may be arrayed either as single clones, each with different insertions, or as sets of pooled clones. That is, as many clones as will represent insertions into essentially every gene in the genome are grown in sets of a defined number. For example, 100,000 clones can be arrayed in 2,000 sets of 50 clones. This can be accomplished by titrating the number of VICTR retroviral particles added to each well of 96-well tissue culture plates. Two thousand clones will fit on approximately 20 such plates. The number of clones may be dictated by the estimated number of genes in the genome of the cells being used. For example, there are approximately 100,000 genes in the genome of mouse ES cells. Therefore, a Library of mutations in essentially every gene in the mouse genome may be arrayed onto 20 96-well plates.

To find an individual clone of interest in the Library arrayed in this manner, reverse transcription-polymerase chain reactions (RT-PCR) are performed on mRNA isolated from pooled clones as presented in FIG. 4. One primer for RT-PCR is anchored in the gene trap vector, i.e. a puro exon-specific oligonucleotide. The other primer is located in the cDNA sequence of a gene of interest. The only way that these two sequences can be juxtaposed to give a positive RT-PCR result (i.e. double stranded DNA fragment visible by agarose gel electrophoresis, as will be familiar to anyone practiced in the art) is by being present in a transcript from a gene trap event occurring in the gene of interest.

For example, if one wishes to obtain an ES cell clone with a mutation in the p53 gene, PCR primers are designed that correspond to the puro and p53 genes. If a VICTR trapping vector integrates into the p53 locus and results in the formation of a fusion mRNA, this mRNA may be detected by RT-PCR using these specifically designed primer pairs. The sensitivity of detection is adequate to find such an event when positive cells are mixed with a large background of negative cells. The individual positive clones are subsequently identified by first locating the pool of 50 clones in which it resides. This process is described in FIG. 5. The positive pool, once identified, is subsequently plated at limiting dilution (approximately 0.3 cells/well) such that individual clones may be isolated. To find the one positive event in 50 clones represented by this pool, individual clones are isolated and arrayed on a 96-well plate. By pooling in columns and rows, the positive well containing the positive clone can be identified with relatively few RT-PCR reactions.

In addition to RT-PCR, the pools may be screened by hybridization techniques (see generally Sambrook et al., 1989, *Molecular Cloning: H Laboratory Manual 2nd edition,* Cold Spring Harbor Press, Cold Spring Harbor, and *Current Protocols in Molecular Biology,* 1995, Ausubel et al. eds., John Wiley and Sons). Specific PCR fragments are generated from the mutated genes essentially as described above for the sequencing protocols of the individual clones (first-strand synthesis using RT primed by a random or oligo dT primer that is appended to a specific primer binding site). The gene trap DNA is amplified from the primer sets in the puro gene and the specific sequences appended to the RT primer. If this were done with pools, the resulting pooled set of amplified DNA fragments could be arrayed on membranes and probed by radioactive, or chemically or enzymatically labeled, hybridization probes specific for a gene of interest. A positive radioactive result indicates that the gene of interest has been mutated in one of the clones of the positively-labeled pool. The individual positive clone is subsequently identified by PCR or hybridization essentially as outlined above.

Alternatively, a similar strategy may be used to identify the clone of interest from multiple plates, or any scheme where a two or three dimensional array (e.g., columns and rows) of individual clones are pooled by row or by column. For example, 96 well plates of individual clones may be arranged adjacent to each other to provide a larger (or virtual/figurative) two dimensional grid (e.g., four plates may be arranged to provide a net 16×24 grid), and the various rows and columns of the larger grid may be pooled to achieve substantially the same result.

Similarly, plates may simply be stacked, literally or figuratively, or arranged into a larger grid and stacked to provide three dimensional arrays of individual clones. Representative pools from all three planes of the three dimensional grid may then be analyzed, and the three positive pools/planes may be aligned to identify the desired clone. For example, ten 96 well plates may be screened by pooling the respective rows and columns from each plate (a total of 20 pools) as well as pooling all of the clones on each specific plate (10 additional pools). Using this method, one may effectively screen 960 clones by performing PCR on only 30 pooled samples.

The example provided below is merely illustrative of the subject invention. Given the level of skill in the art, one may be expected to modify any of the above or following disclosure to produce insubstantial differences from the specifically described features of the present invention. As such, the following example is provided solely by way of illustration and is not included for the purpose of limiting the invention in any way whatsoever.

6.0. EXAMPLES 6.1. Use of VICTR Series Vectors to Construct a Mouse ES cell Gene Trap Library VICTR 3 was used to gather a set of gene trap clones. A plasmid containing the VICTR 3 cassette was constructed by conventional cloning techniques and designed to employ the features described above. Namely, the cassette contained a PGK promoter directing transcription of an exon that encodes the puro marker and ends in a canonical splice donor sequence. At the end of the puromycin exon, sequences were added as described that allow for the annealing of two nested PCR and sequencing primers. The vector backbone was based on pBluescript KS+ from Stratagene Corporation.

The plasmid construct linearized by digestion with Sca I which cuts at a unique site in the plasmid backbone. The plasmid was then transfected into the mouse ES cell line AB2.2 by electroporation using a BioRad GENEPULSER® (electroporator) apparatus. After the cells were allowed to recover, gene trap clones were selected by adding puromycin to the medium at a final concentration of 3 $\mu$g/mL. Positive clones were allowed to grow under selection for approximately 10 days before being removed and cultured separately for storage and to determine the sequence of the disrupted gene.

Total RNA was isolated from an aliquot of cells from each of 18 gene trap clones chosen for study. Five micrograms of this RNA was used in a first strand cDNA synthesis reaction using the "RS" primer. This primer has unique sequences (for subsequent PCR) on its 5' end and nine random nucleotides or nine T (thymidine) residues on it's 3' end. Reaction products from the first strand synthesis were added directly to a PCR with outer primers specific for the engineered sequences of puromycin and the "RS" primer. After amplification, an aliquot of reaction products were subject to a second round of amplification using primers internal, or nested, relative to the first set of PCR primers. This second amplification provided more reaction product for sequencing and also provided increased specificity for the specifically gene trapped DNA.

The products of the nested PCR were visualized by agarose gel electrophoresis, and seventeen of the eighteen clones provided at least one band that was visible on the gel with ethidium bromide staining. Most gave only a single band which is an advantage in that a single band is generally easier to sequence. The PCR products were sequenced directly after excess PCR primers and nucleotides were removed by filtration in a spin column (CENTRICON-100®, Amicon). DNA was added directly to dye terminator sequencing reactions (purchased from ABI) using the standard M13 forward primer a region for which was built into the end of the puro exon in all of the PCR fragments. Thirteen of the seventeen clones that gave a band after the PCR provided readable sequence. The minimum number of readable nucleotides was 207 and some of the clones provided over 500 nucleotides of useful sequence.

Sample data from this set of clones is presented in FIG. 6. Only a portion of sequence (nucleotide or putative amino acid) for 9 Library clones obtained by the methods described in this invention are presented. Under each sequence fragment in the figure is aligned a homologous sequence that was identified using the BLAST (basic local alignment search tool) search algorithm (Altschul et al., 1990, J. Mol. Biol. 215:403–410).

In addition to known sequences, many new genes were also identified. Each of these sequences is labeled "OST" for "Omnibank Sequence Tags." OMNIBANK™ shall be the trademark name for the Libraries generated using the disclosed technology.

These data demonstrate that the VICTR series vectors may efficiently trap genes, and that the procedures used to obtain sequence are reliable. With simple optimization of each step, it is presently possible to mutate every gene in a given population of cells, and obtain sequence from each of these mutated genes. The sample data provided in this example represents a small fraction of an entire Library. By simply performing the same procedures on a larger scale (with automation) a Library may be constructed that collectively comprises and indexes mutations in essentially every gene in the genome of the target cell.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What is claimed is:

1. A collection of cultured eucaryotic cells made by a process comprising:

a) treating a first group of cells with a first vector to stably integrate into the genome of said cells, said first vector mediates the splicing of a foreign exon internal to a cellular transcript and said first vector comprising:
- a foreign exon;
- a splice acceptor site operatively positioned 5' to the initiation codon of said foreign exon;
- a splice donor site operatively positioned 3' to said foreign exon; and
- a sequence comprising a nested set of stop codons in each of the three reading frames located between the end of said foreign exon and said splice donor site;
- said vector not comprising a polyadenylation site operatively positioned 3' to the coding region of said foreign exon; and
- said vector not comprising a promoter element operatively positioned 5' to the coding region of said foreign exon;

b) treating a second group of cells with a second vector to stably integrate into the genome of said cells, said second vector mediates the splicing of a foreign exon 5' to an exon of a cellular transcript and said second vector comprising
- a foreign exon;
- a promoter element operatively positioned 5' to said foreign exon;
- a first splice donor site operatively positioned 3' to said foreign exon;
- an exon comprising a second splice donor site upstream from said promoter and a splice acceptor upstream from said second splice donor site; and
- said vector not comprising a transcription terminator or polyadenylation site operatively positioned relative to the coding region of said foreign exon; and
- said vector not comprising a splice acceptor site operatively positioned between said promoter element and the initiation codon of said foreign exon; and c) selecting for cells from the first group of cells and/or the second group of cells that express the products encoded by the foreign exon;

whereby in the method a collection of cultured eucaryotic cells is made.

2. The collection of cultured eucaryotic cells according to claim 1 wherein said treating of said first group and said second group of cells comprises transfection.

3. The collection of cultured eucaryotic cells according to claim 1 wherein said treating of said first group and said second group of cells comprises infection.

4. The collection of cultured eucaryotic cells according to any one of claims 1 through 3 wherein cells used to make said collection of cultured eucaryotic cells are animal cells.

5. The collection of cultured eucaryotic cells according to claim 4 wherein said animal cells are mammalian cells.

6. The collection of cultured eucaryotic cells according to claim 5 wherein said mammalian cells are rodent cells.

7. The collection of cultured eucaryotic cells according to claim 1 that is organized into individual clones.

8. A method of screening the individual mutant cell clones of claim 7 comprising:
 a) pooling samples of mutant cell clones; and
 b) selecting for transduced cells that express the products encoded by the foreign exons,
 whereby in the method the individual mutant cell clones are screened.

9. A vector for inserting a foreign exon internal to an animal cell transcript, comprising:
 a) a foreign exon;
 b) a splice acceptor site operatively positioned 5' to the initiation codon of said foreign exon;
 c) a splice donor site operatively positioned 3' to said foreign exon; and
 d) a sequence comprising a nested set of stop codons in each of the three reading frames located between the end of said foreign exon and said splice donor site;
 e) said vector not comprising a polyadenylation site operatively positioned 3' to the coding region of said foreign exon; and
 f) said vector not comprising a promoter element operatively positioned 5' to the coding region of said foreign exon.

10. A collection of cultured embryonic stem cells wherein
 a) each cell has a vector integrated into its genome, said vector comprising nested stop codons, a foreign exon and a splice donor site;
 b) the cells of said collection are physically separated so that clonally derived colonies of cells are created;
 c) at least about 200 base pairs of a cellular sequence trapped with said vector from at least about 96 of said colonies have been determined; and
 d) said collection of embryonic stem cells comprises at least about 96 of said colonies of cells; and
 wherein the cultured embryonic stem cells are derived from mouse, rat or human.

11. A method of generating a collection of cultured embryonic stem cells comprising
 a) integrating into the genome of cultured embryonic stem cells a vector, said vector comprising nested stop codons, a foreign exon and a splice donor site;
 b) physically separating said cells, following the integration of said vector, so that at least about 96 clonally derived colonies of cells are created; and
 c) sequencing at least about 200 base pairs of a cellular sequence trapped with said vector from at least about 96 of said colonies; and wherein the cultured embryonic stem cells are derived from mouse, rat or human.

12. A vector for attaching a foreign exon upstream from the 3' end of an animal cell transcript comprising:
 a) a foreign exon;
 b) a promoter element operatively positioned 5' to said foreign exon;
 c) a first splice donor site operatively positioned 3' to said foreign exon;
 d) an exon comprising a second splice donor site upstream from said promoter and a splice acceptor upstream from said second splice donor site; and
 e) said vector not comprising a transcription terminator or polyadenylation site operatively positioned relative to the coding region of said foreign exon; and
 f) said vector not comprising a splice acceptor site operatively positioned between said promoter element and the initiation codon of said foreign exon.

13. A viral vector for attaching a foreign exon upstream from the 3' end of an animal cell transcript comprising:
 a) a foreign exon;
 b) a promoter element operatively positioned 5' to said foreign exon;
 c) a splice donor site operatively positioned 3' to said foreign exon;
 d) an exon comprising a polyadenylation site upstream from said promoter and a splice acceptor upstream from said polyadenylation site; and
 e) said vector not comprising a transcription terminator or polyadenylation site operatively positioned relative to the coding region of said foreign exon; and
 f) said vector not comprising a splice acceptor site operatively positioned between said promoter element and the initiation codon of said foreign exon.

14. The vector of claim 13 wherein said exon additionally comprises stop codons in all three reading frames.

15. A method of using the vector of claim 9 to produce a collection of mutated animal cells comprising:
 a) treating a group of cells to stably integrate a vector according to claim 9; and
 b) selecting for transduced cells that express the products encoded by the foreign exon;
 whereby in the method a collection of mutated animal cells is produced.

16. A vector according to any one of claims 9 or 12 wherein said vector is a viral vector.

17. A vector according to claim 16 wherein said viral vector is a retroviral vector.

18. A collection of cultured animal cells that stably integrate vectors according to claims 9 or 12.

19. A method of using the vector of claim 12 to produce a collection of mutated animal cells comprising:
 a) treating a group of cells to stably integrate a vector according to claim 12; and
 b) selecting for transduced cells that express the products encoded by the foreign exon;
 whereby in the method a collection of mutated animal cells is produced.

20. A collection of cultured embryonic stem cells wherein
 a) each cell has a vector according to any one of claim 9 and 12–14 integrated into its genome;
 b) the cells of said collection are physically separated so that clonally derived colonies of cells are created;

c) at least about 200 base pairs of a cellular sequence trapped with said vector from at least about 96 of said colonies have been determined; and d) said collection of embryonic stem cells comprises at least about 96 of said colonies of cells; and wherein the cultured embryonic stem cells are derived from mouse, rat or human.

21. A collection of cultured embryonic stem cells wherein a) each cell of a first group of cells has a vector according to any one of claims 9 and 12–14 integrated into its genome;

b) each cell of a second group of cells has a vector according to any one of claims 9 and 12–14, but different from the vector integrated into the genome of cells of said first group of cells, integrated into its genome;

c) the cells of said collection are physically separated so that clonally derived colonies of cells are created;

d) at least about 200 base pairs of a cellular sequence trapped with said vector from at least about 96 of said colonies have been determined; and e) said collection of embryonic stem cells comprises at least about 96 of said colonies of cells; and wherein the cultured embryonic stem cells are derived from mouse, rat or human.

22. A method of generating a collection of cultured embryonic stem cells comprising a) integrating into the genome of cultured embryonic stem cells a vector according to any one of claims 9 and 12–14, b) physically separating said cells, following the integration of said vector, so that at least about 96 clonally derived colonies of cells are created; and c) sequencing at least about 200 base pairs of a cellular sequence trapped with said vector from at least about 96 of said colonies; and wherein the cultured embryonic stem cells are derived from mouse, rat or human.

23. A method of generating a collection of cultured embryonic stem cells comprising a) integrating into the genome of a first group of cultured embryonic stem cells a vector according to any one of claims 9 and 12–14;

b) integrating into the genome of a second group of cultured embryonic stem cells a vector according to any one of claims 9 and 12–14, but different from the vector integrated into the genome of cells of said first group of cells;

c) physically separating said cells, following the integration of said vector, so that at least about 96 clonally derived colonies of cells are created; and d) sequencing at least about 200 base pairs of a cellular sequence trapped with said vector from at least about 96 of said colonies; and wherein the cultured embryonic stem cells are derived from mouse, rat or human.

* * * * *

UNITED STATES PATENT AND TRADEMARK OFFICE
CERTIFICATE OF CORRECTION

PATENT NO. : 6,136,566
DATED : October 24, 2000
INVENTOR(S) : Arthur Sands et al.

It is certified that error appears in the above-identified patent and that said Letters Patent is hereby corrected as shown below:

Title page, item [73],
"Assignee: Lexicon Graphics Incorporated, The Woodlands, Tex."
should read
--Assignee: Lexicon Genetics Incorporated, The Woodlands, Tex.--

Title page, item [56],
"Wang et al. High frequency recombination between IoxP sites"
should read
--Wang et al. High frequency recombination between loxP sites--

Title page, item [56],
"Haas et al. TnMax-a versatile minitransposon for teh analysis"
should read
--Haas et al. TnMax-a versatile minitransposon for the analysis--

Signed and Sealed this

Eighth Day of May, 2001

*Attest:*

NICHOLAS P. GODICI

*Attesting Officer*      *Acting Director of the United States Patent and Trademark Office*